US011657636B2

(12) United States Patent
Zou et al.

(10) Patent No.: US 11,657,636 B2
(45) Date of Patent: May 23, 2023

(54) HUMAN PRESENCE DETECTOR AND HUMAN PRESENCE DETECTION METHOD THEREOF

(71) Applicant: Gaodi Zou, Shenzhen (CN)

(72) Inventors: Gaodi Zou, Shenzhen (CN); Xin Zou, Shenzhen (CN); Mingzhi Zou, Shenzhen (CN)

(73) Assignee: Gaodi Zou, Guangdong (CN)

( * ) Notice: Subject to any disclaimer, the term of this patent is extended or adjusted under 35 U.S.C. 154(b) by 962 days.

(21) Appl. No.: 16/273,168

(22) Filed: Feb. 12, 2019

(65) Prior Publication Data

US 2020/0074163 A1 Mar. 5, 2020

(30) Foreign Application Priority Data

Aug. 31, 2018 (CN) .......................... 201811010625.0

(51) Int. Cl.
*G06V 40/10* (2022.01)
*G01J 5/00* (2022.01)
(Continued)

(52) U.S. Cl.
CPC .......... *G06V 40/103* (2022.01); *G01J 5/0025* (2013.01); *G01S 7/415* (2013.01); *G01S 13/56* (2013.01); *G01S 13/581* (2013.01); *A61B 5/0205* (2013.01); *A61B 5/0507* (2013.01); *A61B 2562/0228* (2013.01)

(58) Field of Classification Search
CPC ..... G06K 9/00369; G01S 7/415; G01S 13/02; G01S 13/56; G01S 13/581; G01S 13/88; G01S 13/42; G01J 5/0025; A61B 5/0507; A61B 5/1102; A61B 5/1114; A61B 5/113; A61B 5/1135; A61B 5/7225; A61B 5/024; A61B 5/0205; A61B 5/0816;
(Continued)

(56) References Cited

U.S. PATENT DOCUMENTS 6,281,599 B1 * 8/2001 Murakami .............. B60R 25/24
340/426.36
10,310,073 B1 * 6/2019 Santra .................. A61B 5/0816
(Continued)

*Primary Examiner* — Olumide Ajibade Akonai
(74) *Attorney, Agent, or Firm* — Raymond Y. Chan; David and Raymond Patent Firm

(57) ABSTRACT

A human presence detector includes a microwave generator, a microwave receiver, a frequency mixing wave detector and a signal processor. The microwave generator is configured to emit and transmit a detecting microwave in a detection space. The microwave receiver is configured to receive a corresponding echo of the detecting microwave. The frequency mixing wave detector, linked to the microwave generator and the microwave receiver, is configured to perform a frequency mixing wave detection on the detecting microwave and the corresponding echo of the detecting microwave to output a primary detecting signal. The signal processor linked to the frequency mixing wave detector is configured to select a fluctuation signal at a predetermined frequency range in the primary detecting signal to amplify and output a secondary detecting signal. Accordingly, in response to the detection of the motion at the predetermined frequency range, a human (living) body is detected and determined in the detection space.

17 Claims, 8 Drawing Sheets

(51) Int. Cl.
  *G01S 13/56* (2006.01)
  *G01S 7/41* (2006.01)
  *G01S 13/58* (2006.01)
  *A61B 5/0205* (2006.01)
  *A61B 5/0507* (2021.01)

(58) Field of Classification Search
  CPC ........ A61B 5/02444; A61B 2562/0228; A61B 5/721; F24F 11/30; F24F 2120/10
  See application file for complete search history.

(56) References Cited

U.S. PATENT DOCUMENTS

| | | | |
|---|---|---|---|
| 10,729,333 B2* | 8/2020 | Sullivan | A61B 5/024 |
| 11,202,585 B2* | 12/2021 | Zhang | A61B 5/0205 |
| 2014/0058255 A1* | 2/2014 | Mase | G01S 13/56 |
| | | | 600/430 |
| 2014/0128748 A1* | 5/2014 | Horng | G01S 13/88 |
| | | | 600/484 |
| 2016/0310044 A1* | 10/2016 | Maeno | A61B 5/7221 |
| 2018/0120420 A1* | 5/2018 | McMahon | G01S 13/87 |
| 2018/0184932 A1* | 7/2018 | Saunamaki | G16H 40/40 |
| 2018/0289332 A1* | 10/2018 | Yamaji | A61B 5/0507 |
| 2019/0076084 A1* | 3/2019 | Kanegae | A61B 5/02405 |
| 2020/0317207 A1* | 10/2020 | Sloushch | G01S 13/88 |

\* cited by examiner

HUMAN PRESENCE DETECTOR AND HUMAN PRESENCE DETECTION METHOD THEREOF

CROSS REFERENCE OF RELATED APPLICATION

This is a non-provisional application that claims the benefit of priority under 35U.S.C. § 119 to a Chinese patent application, application number CN201811010625.0, filed Aug. 31, 2018.

NOTICE OF COPYRIGHT

A portion of the disclosure of this patent document contains material which is subject to copyright protection. The copyright owner has no objection to any reproduction by anyone of the patent disclosure, as it appears in the United State Patent and Trademark Office patent files or records, but otherwise reserves all copyright rights whatsoever.

BACKGROUND OF THE PRESENT INVENTION

Field of Invention

The present invention relates to the field of sensing and detection, and more particularly to a human presence detector and its human presence detection method for detecting, utilizing the principle of microwave Doppler effect, the presence of a human being within a detection space.

Description of Related Arts

There are two mainstream conventional techniques for detecting or sensing of human body, one is the detection technology based on the image data (including images and videos) recognition and the other is the detection technology based on the thermal infrared pyroelectric imaging.

Using image processing technologies (such as frame subtraction, background subtraction, and optical flow), the image-recognition-based detection technology is intended to detect a human body as well as the movements of the detected human body from the captured images based on the color and contour of the detected human body. The image recognition technology based on visible light is widely used in the fields of photography, autonomous driving, robotics, medicine and security. However, such image-recognition-based detection technology based on visible light has many limitations.

First of all, the image-recognition-based detection technology is greatly affected by the lighting condition. When the ambient light is not intensive enough, it is difficult to implement human body recognition and detection. Even if the imaging light is supplemented by an additional illumination device, it still requires considering and control the influence of imaging and interference due to the natural light. Moreover, it is difficult to detect and recognize a stationary human body by means of the image-recognition-based detection technology. Also, since the image-recognition-based detection technology relies on specific computing algorithm, it is difficult to recognize and identify a camouflage target. In addition, according to the current technique, the conventional image-recognition-based detection technology based on visible light is unable to detect and monitor subtle movements (minor movements) of the detected human body, i.e. dynamic physiological signals of the human body, such as breathing and heartbeat.

Compared with the image-recognition-based detection technology based on visible light, the detection technology based on the thermal infrared pyroelectric imaging has the advantages of good penetrability, strong anti-interference ability and strong camouflage target recognition ability. However, similar to the image-recognition-based detection technology, the detection technology based on the thermal infrared pyroelectric imaging is also unable to detect and monitor the subtle movements of the detected human body, i.e. dynamic physiological signals of the human body, such as breathing and heart-beating rate.

In addition, since all living organisms would generate infrared radiation, it is necessary to take consideration of the interference of such infrared radiation from other living organisms when implementing the detection technology for human presence based on the thermal infrared pyroelectric imaging. Further, in man-made buildings, heat generated by any artificial equipment may also affect the detection result or cause interference.

Moreover, the data obtained either by the detection technology for human presence based on the image recognition or the detection technology for human presence based on the thermal infrared pyroelectric imaging contain a lot of privacy information. This is one of the reasons that why the conventional human presence detection technology has not been popularized. For example, many users do not like to use the camera as a human presence detector because it is worried that importance images might be illegally recorded and/or used. Further, due to the energy and sensitivity issues, the conventional human presence detection technology, either based on the image data recognition or based on the thermal infrared pyroelectric imaging, is merely adapted in scientific and military applications.

It is also worth mentioning that the human presence detection contains two-stage analysis in the conventional human presence detection technology, either based on the image recognition or based on the thermal infrared pyroelectric imaging. The first stage is to capture the image data and the second stage is to make a determination based on the image data. Accordingly, the sharpness and resolution of the image must be guaranteed. And, as it is well known, the technology of image recognition has a long way to go to enhance its recognition accuracy, which would cost a relatively heavy research cost.

The detection of the human presence provides very important information. Utilizing this information, some electrical appliances or services can intelligently adjust and improve its operation mode. However, there is no reliable sensor or detector that can meet the requirement of the current market.

In general, the conventional human body presence detection technology is mainly based on human body motion and/or image data recognition, which is vulnerable to various environmental factors.

SUMMARY OF THE PRESENT INVENTION

The invention is advantageous in that it provides a human presence detector and a human presence detection method thereof, which is able to directly obtain the data regarding the presence of a human body, such that the conventional subsequent complex analysis is eliminated, and the efficiency of usage the human presence data is enhanced.

Another advantage of the invention is to provide a human presence detector and a human presence detection method thereof, which is able to exclusively obtain the human presence data of a human (living) body, i.e. to detect the actual user to be detected or the one who is experiencing the detection.

Another advantage of the invention is to provide a human presence detector and a human presence detection method thereof, which can obtain the human presence data among objects without complicated data processing for further determination of human (living) body.

Another advantage of the invention is to provide a human presence detector and a human presence detection method thereof, wherein the human presence detector is able to detect the presence of any human body within a detection space.

Another advantage of the invention is to provide a human presence detector and a human presence detection method thereof, wherein, by utilizing the principle of microwave Doppler effect, the detector is able to determine the presence of a human (living) body in responsive to the movement and/or the subtle movements of the human body.

Another advantage of the invention is to provide a human presence detector and a human presence detection method thereof, wherein the human presence detector comprises a microwave generator and a microwave receiver, wherein the microwave generator is configured to transmit a detecting microwave in a detection space, and the microwave receiver is arranged to receive the corresponding echo of the detecting microwave, wherein in response to detecting a phase difference between the detecting microwave and the corresponding echo of the detecting microwave, the human presence detector determines whether a human (living) body is presented in the detection space.

Another advantage of the invention is to provide a human presence detector and a human presence detection method thereof, wherein the human presence detector further comprises a frequency mixing wave detector which is configured to be capable of performing a frequency mixing wave detection on the detecting microwave emitted by the microwave generator and the corresponding echo of the detecting microwave received by the microwave receiver so as to output a corresponding primary detecting signal which is a response in responsive to the motion, such as movement, action or the like, within the detection space, wherein if a fluctuation signal with a predetermined frequency is contained in the primary detecting signal, the human presence detector determines that a human body (living body) is presented in the detection space.

Another advantage of the invention is to provide a human presence detector and a human presence detection method thereof, wherein the human presence detector further comprises a signal processor which is configured to select and amplify the primary detecting signal outputted from the mixing detector adapted for selecting a fluctuation signal, having a predetermined frequency range, from the primary detecting signal to amplify and output a secondary detection signal. In other words, the human presence detector amplifies the fluctuation signal in responsive to the motion(s) at the predetermined frequency range in the detection space, so as to determine the presence of human (living) body in responsive to the motions within the predetermined frequency range. Another advantage of the invention is to provide a human presence detector and a human presence detection method thereof, wherein the signal processor is configured to pick up a fluctuation signal with a frequency less than 3 Hz to amplify and output a secondary detection signal, while the fluctuation signal with a frequency greater than 3 Hz is filtered from the primary detection signal. In other words, the secondary detection signal is a response signal corresponding to the motion(s), action(s) or movement(s) with a frequency less than 3 Hz (three times per second), such that the interference of other motion(s), action(s) or movement(s) having a frequency greater than 3 Hz occurred in the detection space can be substantially avoided.

Another advantage of the invention is to provide a human presence detector and a human presence detection method thereof, wherein the human presence detector determines a presence of human (living) body in response to a detection of a motion signal with a frequency less than 3 Hz (three times per second) within the detection space. It is worth mentioning that the frequency of the motion(s), action(s) or movement(s) occurred in the natural environment is mainly greater than 3 Hz (three times per second), so that the human presence detector disclosed in this application is able to reduce the interference of environmental motions, actions or movements in the detection space, resulting in enhancing the detection accuracy.

Another advantage of the invention is to provide a human presence detector and a human presence detection method thereof, wherein the human presence detector determines a presence of human (living) body in response to a detection of a motion signal with a frequency less than 3 Hz (three times per second) within the detection space. It is worth mentioning that the frequency of the motion occurred in the natural environment are mainly greater than 3 Hz (three times per second), so that the signal processor is less possible to be interfered by the electromagnetic interference signals in the natural environment, resulting in more stable output of the secondary detection signal.

Another advantage of the invention is to provide a human presence detector and a human presence detection method thereof, wherein the human presence detector is configured to determine a presence of human (living) body in response to a human respiratory motion and/or a heartbeat motion with a frequency less than 3 Hz (three times per second), so as to reduce the interference of the environmental motions, actions or movements on the detection results.

Another advantage of the invention is to provide a human presence detector and a human presence detection method thereof, wherein the human presence detector is able to determine a presence of the human (living) body in response to the respiratory motion and/or a heartbeat motion in real-time based on the principle of microwave doppler effect, such that while the human presence detector is responding to the respiratory motion and/or a heartbeat motion to determine the presence of the human (living) body to be detected, it is able to detect and determine the condition and status of the breathing and/or heartbeat of the human body to be detected in the detection space.

Another advantage of the invention is to provide a human presence detector and a human presence detection method thereof, wherein since the amplitude intervals and the frequency intervals of the fluctuation signals corresponding to the breathing and heartbeat of different human (living) bodies are different, the fluctuation signals corresponding to the breathing and heartbeat of different human (living) bodies in the detection space can be separated, so that the number of the human bodies within the detection space can thus be obtained while monitoring the respiratory motions and/or heartbeat motions of multiple human bodies to be detected in the detection space at the same time.

Another advantage of the invention is to provide a human presence detector and a human presence detection method thereof, wherein according to the different amplitude intervals and the frequency intervals of the fluctuation signals corresponding to the respiratory motions and/or heartbeat motions of different human (living) bodies, the fluctuation signals corresponding to the respiratory motion and/or heartbeat motion of a specific human being in the detection space can be identified and separated, so that the human presence detector can monitor the condition and status of the breathing and/or heartbeat of the specific human body detected in the detection space according to the amplitude and frequency of the identified and separated fluctuation signal.

Another advantage of the invention is to provide a human presence detector and a human presence detection method thereof, wherein the human presence detector is able to detect or monitor the respiratory motions and/or heartbeat motions of the human body detected in the detection space in a real time basis. In particular, the human presence detector is able to monitor the respiratory motions of the detected human (living) body so as to determine the health status of the detected human being (or human body).

Another advantage of the invention is to provide a human presence detector and a human presence detection method thereof, wherein the processing of the secondary detection signal can be delayed, that is according to the cyclical and periodic characteristic of the fluctuation signal corresponding to respiratory and heartbeat motions of the human body, the interference of sporadic motions with a frequency less than 3 Hz with respect to the waveform of the secondary detection signal is eliminated, thereby improving the reliability of the detection on the human body's breathing and/or heartbeat condition and status.

Another advantage of the invention is to provide a human presence detector and a human presence detection method thereof, wherein the human presence detector is able to detect whether there is a human body presence within a detection space.

Another advantage of the invention is to provide a human presence detector and a human presence detection method thereof, wherein the human presence detection method is adapted for determining the presence of a human (living) body in responsive to a movement or subtle movement of the human body based on the microwave Doppler effect.

Another advantage of the invention is to provide a human presence detector and a human presence detection method thereof, wherein detecting microwave is transmitted into a detection space and the corresponding echo of the detecting microwave is received, wherein when there is a phase difference between the detecting microwave and the corresponding echo of the detecting microwave, a presence of a human (living) body in the detection space is determined.

Another advantage of the invention is to provide a human presence detector and a human presence detection method thereof, wherein the detecting microwave transmitted by the microwave generator and the corresponding echo received by the microwave receiver perform a mixing frequency detection to output a corresponding primary detecting signal, which is a response in responsive to the corresponding motion, action or movement in the detection space, wherein when the primary detecting signal has a fluctuation signal having a predetermined frequency, the presence of a human (living) body is determined.

Another advantage of the invention is to provide a human presence detector and a human presence detection method thereof, wherein by selecting and amplifying the outputted primary detecting signal, a fluctuation signal within a predetermined frequency range in the primary detecting signal is selected to amplify and output a secondary detection signal, that is the fluctuation signal responsive to the motion, action or movement at the predetermined frequency range is amplified for determining the presence of a human body in the detection space in responsive to the motion, action or movement within the predetermined frequency range.

Another advantage of the invention is to provide a human presence detector and a human presence detection method thereof, wherein the presence of human body is determined in responsive to any motion signal with a frequency less than 3 Hz (three times per second) in the detection space. Since the frequency of the motion signals occurred in the natural environment are mainly 3 Hz or more (three times per second), the human presence detection method of the present invention is capable of reducing the interference from the environmental motions, actions and/or movements in the natural environment, so that the detection results are more accurate.

Another advantage of the invention is to provide a human presence detector and a human presence detection method thereof, wherein the presence of human (living) body is determined in responsive to the motion, action or movement with motion frequency less than 3 Hz (three times per second), wherein since the respiratory motion and/or heartbeat motion of a human body is characteristic in having a frequency less than 3 Hz (three times per second), the human presence detection method of the present invention can reduce the interference of the environmental action, motion and/or movement in the detection environment, as well as detect whether there is a presence of human body in the detection space in responsive to the respiratory motion and/or heartbeat motion of human body detection result being detected.

Another advantage of the invention is to provide a human presence detector and a human presence detection method thereof, wherein the human presence detection method, based on the principle of microwave Doppler effect in response to the respiratory or heartbeat motions of the human body in real-time basis, is able to determine the condition and status of the breathing and/or heartbeat of the human body to be detected while monitoring the presence of the human (living) body to be detected in responsive to the respiratory motion and/or heartbeat motion of human body at the same time.

Another advantage of the invention is to provide a human presence detector and a human presence detection method thereof, wherein the human presence detection method is able to detect or monitor the respiratory and heartbeat motions of the detected human body in a real-time basis, so as to determine the breathing and heartbeat condition and status of the detected human being (or human body), so that an alerting signal can be generated in response to an unusual or abnormal breathing and/or heartbeat of the human being (or living body) is occurred in the detection space.

Another advantage of the invention is to provide a human presence detector and a human presence detection method thereof, wherein the data of the respiratory and heartbeat motions of the human body being detected or monitored in real-time can be utilized by other electronic appliances, so as to provide service with artificial intelligence.

Additional advantages and features of the invention will become apparent from the description which follows, and may be realized by means of the instrumentalities and combinations particular point out in the appended claims.

According to the present invention, the foregoing and other objects and advantages are attained by a human presence detector, comprising:

a microwave generator which is configured to emit a detecting microwave transmitting within a detection space;

a microwave receiver which is configured to be able to receive a corresponding echo of the detecting microwave;

a frequency mixing wave detector linked to the microwave generator and the microwave receiver and being configured to be able to perform a frequency mixing wave detection on the detecting microwave emitted from the microwave generator and the corresponding echo of the detecting microwave received by the microwave receiver, so as to output a primary detecting signal correspondingly, wherein the primary detecting signal is a response signal of at least a motion, action, or movement detected in the corresponding detection space; and a signal processor linked to the frequency mixing wave detector and being configured to be able to select and amplify the primary detecting signal outputted by the mixing detector, so as to select a fluctuation signal, having a predetermined frequency range, from the primary detecting signal to amplify and output a secondary detecting signal, thereby the response signal corresponding to the motion, action or movement detected in the detection space, having the predetermined frequency range, is amplified by means of the human presence detector for determining a presence of a human (living) body within the detection space by responding to motion, action or movement thereof having the predetermined frequency range.

In one embodiment of the present invention, the signal processor is configured to select a fluctuation signal at a frequency less than 3 Hz from the primary detecting signal to amplify and to output a secondary detecting signal at a frequency less than 3 Hz, wherein the fluctuation signal at a frequency greater than 3 Hz in the primary detecting signal is filtered from the primary detecting signal so as to output the secondary detecting signal with fluctuation signal frequency at 3 Hz or less, wherein the secondary detecting signal is a response signal merely in responsive to the motion, action or movement at a frequency less than 3 Hz detected in the detection space, so as to avoid any interference of any motion having a frequency greater than 3 Hz occurred in the detection space.

In one embodiment of the present invention, the microwave generator and the microwave receiver are configured together as a microwave sensor adapted to emit and transmit the detecting microwave and receive the corresponding echo of the detecting microwave.

In one embodiment of the present invention, the mixing detector is integrated in the microwave sensor.

According to another aspect of the present invention, it further provides a human presence detector which comprises:

a microwave sensor which is configured to emit and transmit a detecting microwave within a detection space and to receive a corresponding echo of the detecting microwave, wherein the microwave sensor is further configured to perform a frequency mixing wave detection on the detecting microwave emitted by the microwave generator and the corresponding echo of the detecting microwave received by the microwave receiver, so as to output a primary detecting signal correspondingly; and a signal processor linked to the microwave sensor and configured to select and amplify the primary detecting signal outputted by microwave sensor, in order to select a fluctuation signal within a predetermined frequency range from the primary detecting signal to amplify and output a secondary detecting signal, thereby response signal of action, motion or movement detected in the detection space having motion frequency within the predetermined frequency range is amplified. In other words, the secondary detecting signal only in response to action, motion or movement having motion frequency within the predetermined frequency range, so that the human presence detector can determine a presence of a human (living) body in the detection space in responsive to the action, motion or movement of the human (living) body within the predetermined frequency range.

According to another aspect of the present invention, it further provides a human presence detection method, comprising the following steps.

(a) transmitting a detecting microwave in a detection space;

(b) receiving a corresponding echo of the detecting microwave;

(c) performing a frequency mixing wave detection on the detecting microwave and the corresponding echo of the detecting microwave and output a primary detecting signal; and (d) selecting a fluctuation signal at a predetermined frequency range in the primary detecting signal to amplify and output a secondary detecting signal.

In one embodiment of the present invention, in the step (d), the predetermined frequency range is less than or equal to 3 Hz, wherein the secondary detecting signal is response signal merely in responsive to actions, motions or movements at a motion frequency less than 3 Hz detected in the detection space.

In one embodiment of the present invention, the method further comprises a step of:

(e) monitoring and detecting any fluctuation signal in the secondary detecting signal, wherein a presence of a human (living) body is determined when one or more fluctuation signals at the predetermined frequency range is detected in the secondary detecting signal. In one embodiment of the present invention, the method further comprises a step of:

(f) identifying and separating the secondary detecting signal for obtaining response signal in responsive to breathing and/or heartbeat frequency in the detection space.

According to another aspect of the present invention, it provides a human presence detector, which comprises a microwave sensor and a signal processor, wherein a detecting microwave emitted and transmitted from the microwave sensor is reflected by a human body and processed by the signal processor, wherein the signal processor is configured to analyze the reflected microwave based on a phrase difference of the detecting microwave emitted by the microwave sensor and the microwave reflected by the human body in order to obtain a detection result for the presence of the human body.

In one embodiment of the present invention, the microwave sensor comprises at least one microwave generator, at least one microwave receiver and a frequency mixing wave detector, wherein the microwave generator is configured to emit and transmit the detecting microwave within a detection space, wherein the microwave receiver is configured to receive a corresponding echo of the detecting microwave, wherein the frequency mixing wave detector, which is linked to the microwave generator and the microwave receiver, is configured to perform a frequency mixing wave detection on the detecting microwave transmitted by the microwave generator and the corresponding echo of the detecting microwave received by the microwave receiver to output the detection result data correspondingly.

In one embodiment of the present invention, the microwave sensor further comprises a power-supply module arranged for acquiring external power source for the microwave generator and the microwave receiver in the human presence detector and a detection module for receiving the reflected microwave as detecting data.

In one embodiment of the present invention, the signal processor further comprises a central control unit and a signal processing module, wherein the signal processing module is arranged for receiving and processing the detecting data to obtain the determinable detection result, wherein the central control unit is prearranged to obtain the detection result and process the program of the detecting data detection result.

In one embodiment of the present invention, the detection module is a microwave-Doppler detection module.

In one embodiment of the present invention, the signal processing module comprises at least one signal amplifying module and at least one wave filter.

In one embodiment of the present invention, the signal processing module comprises at least one DC (Direct Current) amplifying module and at least one wave filter.

In one embodiment of the present invention, the signal processing module comprises at least one AC (Alternating Current) amplifying module and at least one wave filter.

In one embodiment of the present invention, the signal processing module comprises at least one analog wave filter and at least one digital wave filter.

In one embodiment of the present invention, the signal processing module comprises at least one signal amplifying module and at least one analog wave filter.

In one embodiment of the present invention, the signal processing module comprises at least one signal amplifying module and at least one digital wave filter.

In one embodiment of the present invention, the central control unit further comprises a signal sampling module, a digital filtering module, a program center, and at least one inputting and outputting interface, wherein different program instructions for different requirements are stored in the program center, wherein the signal sampling module and the digital filtering module are configured to process the detecting data to obtain the detection result, wherein the program center is preset with requirement for determination, and the inputting and outputting interface processes execution of the detection result.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Those skilled in the art should understand that, in the disclosure of the present invention, terminologies of "longitudinal," "lateral," "upper," "front," "back," "left," "right," "perpendicular," "horizontal," "top," "bottom," "inner," "outer," and etc. just indicate relations of direction or position are based on the relations of direction or position shown in the appended drawings, which is only to facilitate descriptions of the present invention and to simplify the descriptions, rather than to indicate or imply that the referred device or element must apply specific direction or to be operated or configured in specific direction. Therefore, the above-mentioned terminologies shall not be interpreted as confine to the present invention.

It is understandable that the term "a" should be understood as "at least one" or "one or more". In other words, in one embodiment, the number of an element can be one and in other embodiment the number of the element can be greater than one. The term "a" is not construed as a limitation of quantity.

Figure 1:
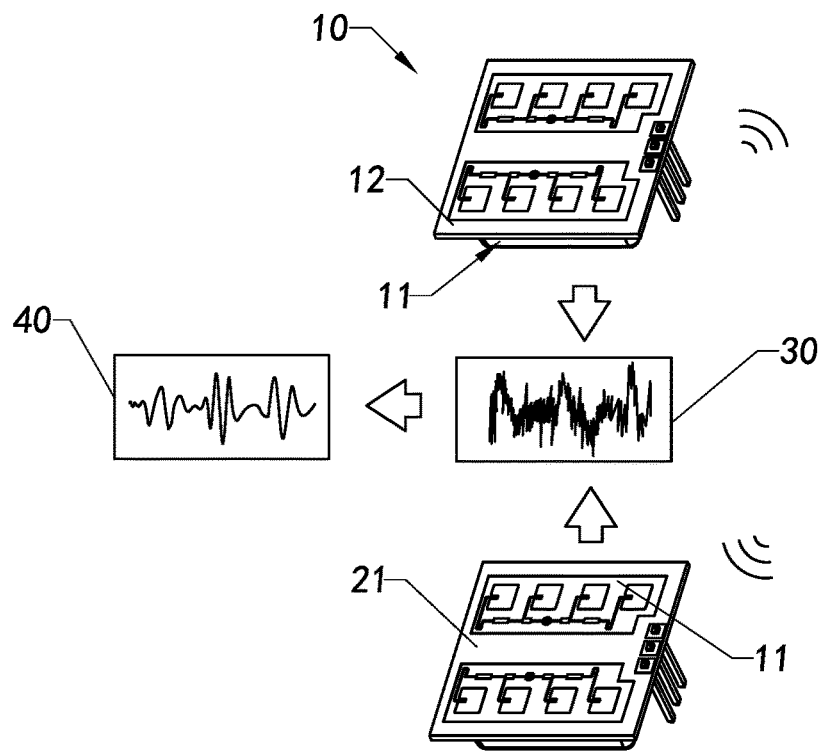
FIG. 1 is a schematic view of a human presence detector according to a preferred embodiment of the present invention.
Figure 2:
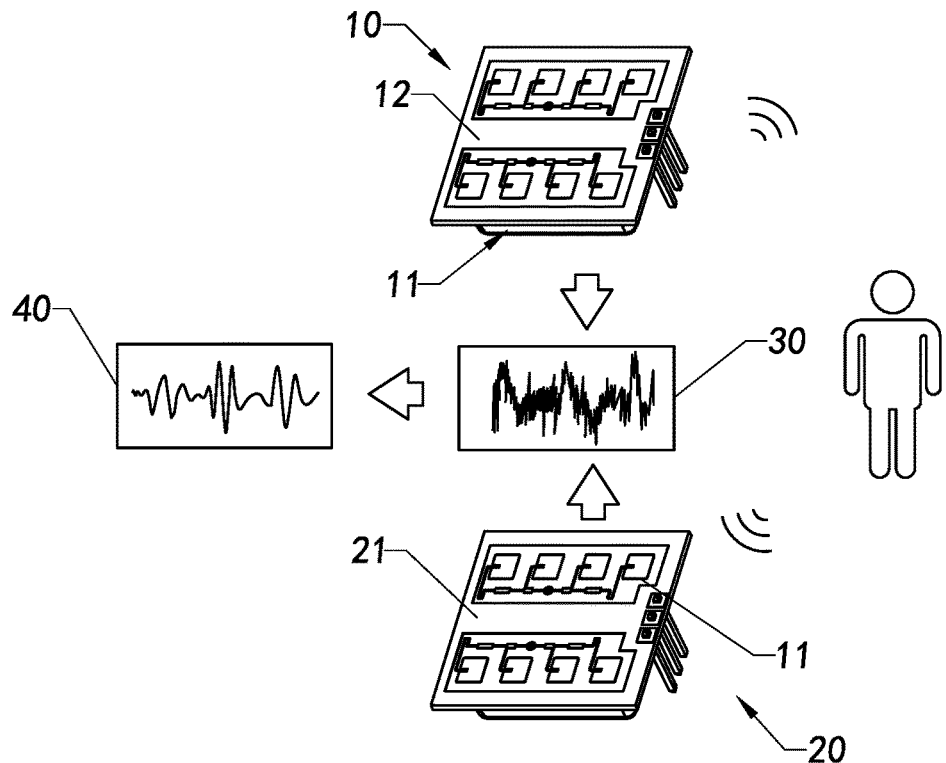
FIG. 2 is a schematic diagram illustrating the detecting of the presence of a human body in a detection space utilizing the human presence detector according to the above preferred embodiment of the present invention.

Referring to FIG. 1 and FIG. 2 of the drawings, a human presence detector according to a preferred embodiment of the present invention is illustrated, wherein the human presence detector comprises at least one microwave generator 10, at least one microwave receiver 20, a frequency mixing wave detector 30, and a signal processor 40. The microwave generator 10 is arranged to emit and transmit a detecting microwave in a detection space. The microwave receiver 20 is arranged to receive a corresponding echo of the detecting microwave, i.e. the detecting microwave reflected by an object, such as a human body, back towards the microwave receiver 20. The frequency mixing wave detector 30 is linked to the microwave generator 10 and the microwave receiver 20 and arranged to perform a frequency mixing wave detection on the detecting microwave emitted by the microwave generator 10 and the corresponding echo received by the microwave receiver 20 and to output a primary detecting signal correspondingly, wherein the primary detecting signal is a response signal of motion (including but not limited to action, motion and/or very small movement of a human (living) body, such as breathing, blinking, heartbeat, spasm, talking, smiling, and etc.) detected in the detection space. The signal processor 40 is linked to the frequency mixing wave detector 30 and arranged to select and amplify the primary detecting signal outputted by the mixing detector 30, wherein the signal processor 40 is configured to select any fluctuation signal having a predetermined frequency range of the primary detecting signal to amplify and output a secondary detecting signal. More specifically, the human presence detector amplifies the response signal in responsive to the motion(s), action(s) and/or movement(s) having the predetermined frequency range detected in the detection space. That is the secondary detecting signal is response signal in response to the motion, action and/or movement having motion frequency within the predetermined frequency range for determining the presence of human (living) body according to the response to one or more motions at the predetermined frequency.

In particular, the predetermined frequency range is embodied as not more than 100 Hz. Preferably, the frequency of the secondary detecting signal is embodied as not more than 3 Hz.

It is worth mentioning that those who skilled in the art would understand that the selection and amplification processing of the primary detecting signal by the signal processor 40 can be implemented by circuit(s) with selecting and processing functions, or by specific program(s) for processing data of the primary detecting signal, or a combination of the above two methods. In other words, within the fundamental scope of the current circuit and methods for signal selection and amplification, the signal selection and amplification of the signal processor 40 is not intended to be limited in the present invention.

In addition, it should be understood that, in order for acquiring the secondary detecting signal at the predetermined frequency range, the signal processor 40 can be configured to perform multistage selection and/or amplification operation(s) to the received primary detecting signal, so as to select any fluctuation signal at the predetermined frequency range in the primary detecting signal to amplify and to output the secondary detecting signal. In other words, a plurality of the signal processors 40 can be used, or alternatively, the signal processor 40 may further comprise of a plurality of signal selection and/or signal processing components, that is not intended to be limiting in the present invention.

It is appreciated that when the signal processor 40 according to the preferred embodiment of the present invention is configured to be able to select the fluctuation signal having a frequency less than 3 Hz from the primary detecting signal to amplify and output, any fluctuation signal having a frequency greater than 3 Hz in the secondary detecting signal will be filtered out so as to select the fluctuation signal with a frequency less than 3 Hz in the primary detecting signal to amplify and output the secondary detecting signal. That is, the secondary detecting signal is a response signal that merely responds to the motion(s) with a motion frequency less than 3 Hz (three times per second) occurred in the detection space, such that such motion(s) detected by the human presence detector of the present invention is highly likelihood to be the motions generated during the breathing and/or heart beating of the detected human body (living body) because that, except for the regular dynamic physiological signals of the human body such as breathing and heartbeat, in the living environment of human beings, it is more rarely to have any motion that is regular or even irregular with low-frequency signals as low as 3 Hz or less.

More specifically, considering the facts that the normal resting breathing frequency of a healthy adult is generally 12 to 24 times per minute and the normal resting breathing frequency of a newborn baby is generally 20 to 45 times per minute while the sickness may cause the respiratory rate to increase or decrease to some extent but still generally maintaining in three times per second or less. That is, the body motion caused during breathing is the motion with a motion frequency less than 3 Hz (three times per second). Therefore, when a regular fluctuation signal at a frequency less than 3 Hz is detected in the secondary detecting signal outputted from the human presence detector, it is a great probability of a presence of a human body in the detection space. Further, as it is well known, the microwave has a good penetrating ability that while the human presence detector is sensitive enough, it is able to detect the fluctuation signal having a frequency of 3 Hz or less in the secondary detecting signal outputted in responsive to the body motion generated during heartbeat (generally no more than 3 times per second) of the detected human body. Therefore, the regular fluctuation signal(s) at a frequency less than 3 Hz in the secondary detecting signal outputted from the signal processor 40 of the human presence detector of the present invention is corresponding to the body motion generated during the breathing or heartbeat of the human (living) body.

Accordingly, the human presence detector of the present invention is to detect the presence of human body in a detection space based on the characteristics of the human body's dynamic physiological signals, such as the respiratory rate or heartbeat rate of the human being. Further, by means of continuous detection, it is able to monitor whether the detected breathing and/or heartbeat of the human body is in a normal status or condition. For example, when the respiratory rate of the human body detected by the human presence detector is less than 12 times per minute (for adult) or larger than 24 times per minute (for adult), the human presence detector may generate an alerting signal to inform the user of the human presence detector or even a doctor that the detected human body is in an abnormal physiological status. Correspondingly, the human presence detector as disclosed in the present invention can be utilized to monitor whether a dynamic physiological signal of a human body is normal or not. Also, after the human presence detector of the present invention detects the presence of a human (living) body, when the human body being detected is experiencing a respiratory or cardiac arrest, the human presence detector of the present invention would generate an alerting signal accordingly.

Those who skilled in the art would know that the microwave has the advantages of insensitivity to micro substance (such as dust, smoke and steam), low airborne loss, good reflection ability, high transmitting speed, high sensing responsive ability and wide sensing range. In addition, the microwave has a Doppler effect. Accordingly, the human presence detector of the present invention that utilizes microwave for detection of human body has various advantages, that the conventional detection (or sensing) of human body based on visible light (image-recognition) and the conventional detection (or sensing) of human body based on thermal infrared (thermal infrared pyroelectric imaging) do not, including, for example, the capability of detecting very subtle movement of the human body, less likely to be influence by the environmental factors and less susceptible to interference to the detection structure, etc.

Alternatively, those who skilled in the art would understand that the microwave generator 10 of the human presence detector of the present invention, beside generating and emitting microwave, can also be configured to receive the corresponding echo of the detecting microwave at the same time. Alternatively, the microwave generator 10 and the microwave receiver 20 of the human presence detector according to the preferred embodiment of the present invention may also be integrally arranged to form an integral microwave sensor adapted to emit and transmit the detecting microwave and receive the corresponding echo of the detecting microwave.

Referring to FIG. 1 of the drawings, the microwave generator 10 according to the preferred embodiment of the present invention further comprises a microwave oscillator 11 and a microwave transmitting antenna 12, wherein the microwave oscillator 11 is configured to generate a detecting microwave signal (electric signal) and the microwave transmitting antenna 12 is configured to transmit a detecting microwave corresponding to the detecting microwave signal. Further, as shown in the FIG. 1 of the drawings, the microwave receiver 20 further comprises a microwave receiving antenna 21 adapted for receiving the corresponding echo of the detecting microwave. Furthermore, the microwave receiving antenna 21 is configured to be able to receive the corresponding echo of the detecting microwave and then convert the corresponding echo of the detecting microwave into an echo signal (electric signal). The frequency mixing wave detector 30 is communicatively linked to the microwave generator 10 and microwave receiver 20 and is configured to perform a frequency mixing wave detection on the detecting microwave and the corresponding echo of the detecting microwave and output the primary detecting signal.

Those who skilled in the art would understand that the microwave is referred to an electromagnetic wave having a frequency from 300 MHz to 300 GHz, wherein the microwave generators 10 and the microwave receivers 20 suitable for different frequency bands are different in the structures and configurations. The main principle in the present invention is to select the fluctuation signal with a predetermined frequency range from the primary detecting signal to amplify and to output the secondary detecting signal having the predetermined frequency range, ensuring the secondary detecting signal is merely responsive to motions having motion frequency at the predetermined frequency range, so that it is enabled to determine the presence and the status of a human (living) body by detecting whether there is any motion having the predetermined frequency range as well as the motion frequency of such motion, wherein structure of the microwave generator 10 and microwave receiver 20 as illustrated in the drawings are for illustrative purposes only, which is not intended to limit the structures of the microwave generate 10 and the microwave receiver 20 of the present invention.

It is appreciated that the frequency mixing wave detector 30 performs the frequency mixing wave detection on the detecting microwave signal and the corresponding echo signal based on the Doppler effect and output the primary detecting signal, wherein the primary detection signal is a response signal in responsive to a motion occurred in the detection space.

Further, the frequency mixing wave detector 30 is linked to the signal processor 40, wherein the signal processor 40 is configured to receive the primary detecting signal and then to select and amplify the primary detecting signal, so as to select the fluctuation signal having the predetermined frequency range from the primary detecting signal to amplify and output a secondary detecting signal, wherein when the signal processor 40 is arranged to filter any fluctuation signal having a frequency greater than 3 Hz in the primary detecting signal, the signal processor 40 is configured to select the fluctuation signal with a frequency equal to or less than 3 Hz to amplify and output, so that in the primary detecting signal, the fluctuation signal generated in response to a motion with a frequency greater than 3 Hz (three times per second) is filtered and the secondary detecting signal outputted by the signal processor 40 is merely response signal in response to motion having motion frequency at 3 Hz (three times per second) or less, and the fluctuation signal in response to the motion having motion frequency equal to or less than 3 Hz (three times per second) in the detection space is amplified. In other words, the human presence detector of the present invention is adapted to amplify the fluctuation signal in response to that motion with a frequency equal to or less than 3 Hz (three times per second), wherein since the motion generated during the human breathing and heartbeat has human (living) body feature and a motion frequency less than 3 Hz, the possibility of having a human (living) body presented in the detection space is very high when the secondary detecting signal contains fluctuation signal at the predetermined frequency range (such as 3 Hz or less).

In particular, when the human (living) body presented in the detection space is detected in a real time mode, the fluctuation signal in the secondary detecting signal is in response to the human motion within the frequency less than 3 Hz (three times per second), and that the regular fluctuation signal in the secondary detecting signal is in high likelihood corresponding to the body motion caused during the breathing and/or heartbeat of the detected human body. In other words, the human presence detector of the present invention is able to detect the presence of a human (living) body based on the breathing motion and/or heartbeat motion of the detected human body while monitoring the physiological status of the breathing and/or heartbeat of the detected human body at the same time.

It is worth mentioning that the human presence detection of the present invention, based on the Doppler effect, the detection in the detection space is implemented through the invisible microwave which produces little radiation to the human body and is more convenience. That is especially meaningful in monitoring the respiratory status and/or heartbeat status in the home environment.

Figure 3:
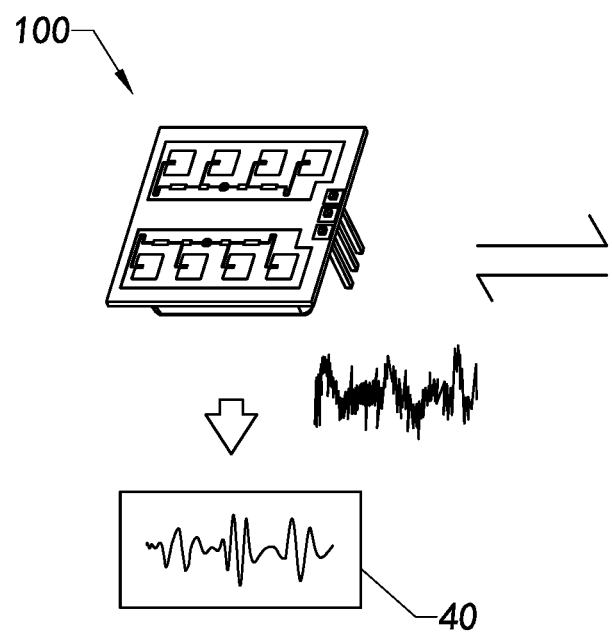
FIG. 3 is a schematic view of a human presence detector according to another preferred embodiment of the present invention.
Figure 4:
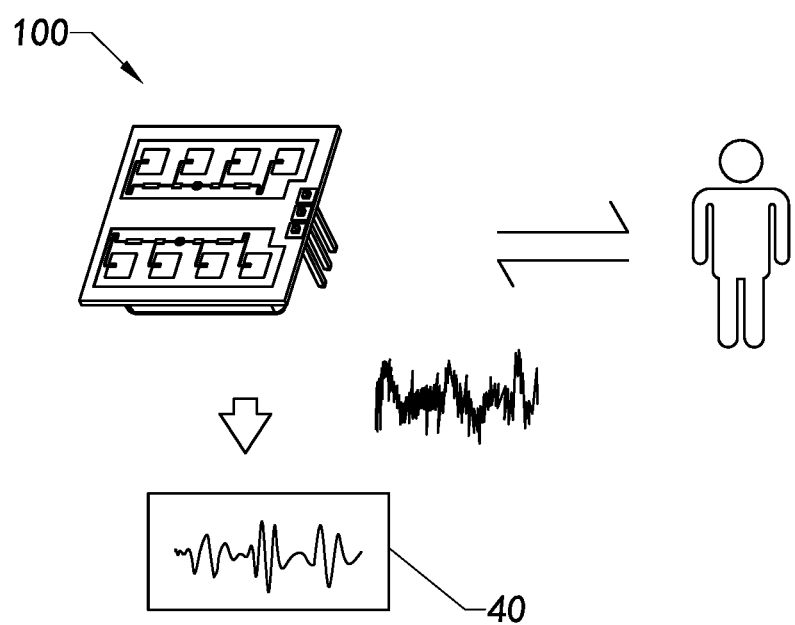
FIG. 4 is a schematic diagram illustrating the detecting of the presence of a human body in a detection space using the human presence detector according to the above another preferred embodiment of the present invention.

Referring to FIG. 3 and FIG. 4 of the drawings, an alternative embodiment of the human presence detector according to the present invention is illustrated, wherein the human presence detector comprises at least one microwave sensor 100 and a signal processor 40 communicatively linked with the microwave sensor 100. The microwave sensor 100 is configured to emit and transmit a detecting microwave within a detection space to receive a corresponding echo of the detecting microwave, and to perform a frequency mixing wave detection on the detecting microwave and the corresponding echo of the detecting microwave so as to output a primary detecting signal. The signal processor 40 is configured to receive the primary detecting signal for selection and amplification, wherein a fluctuation signal at a predetermined frequency range is selected from the primary detecting signal to amplify and output a secondary detecting signal. In particular, the predetermined frequency range is embodied as less than 3 Hz.

In other words, the microwave sensor 100 of the human presence detector according to the preferred embodiment of the present invention is arranged to emit and transmit the detecting microwave, as well as to receive the corresponding echo of the detecting microwave at the same time and to output the primary detecting signal, wherein the signal processor 40 is adapted to select and amplify the primary detecting signal outputted by the microwave sensor 100. It is appreciated that the signal processor 40 can be a programmed or computerized signal processor for selecting and amplifying the primary detecting signal outputted by the microwave sensor 100.

It is worth mentioning that in other embodiments of the present invention, the signal processor 40 can be further integrally configured in the microwave sensor 100, which is not intended to be limiting in the present invention.

Figure 11:
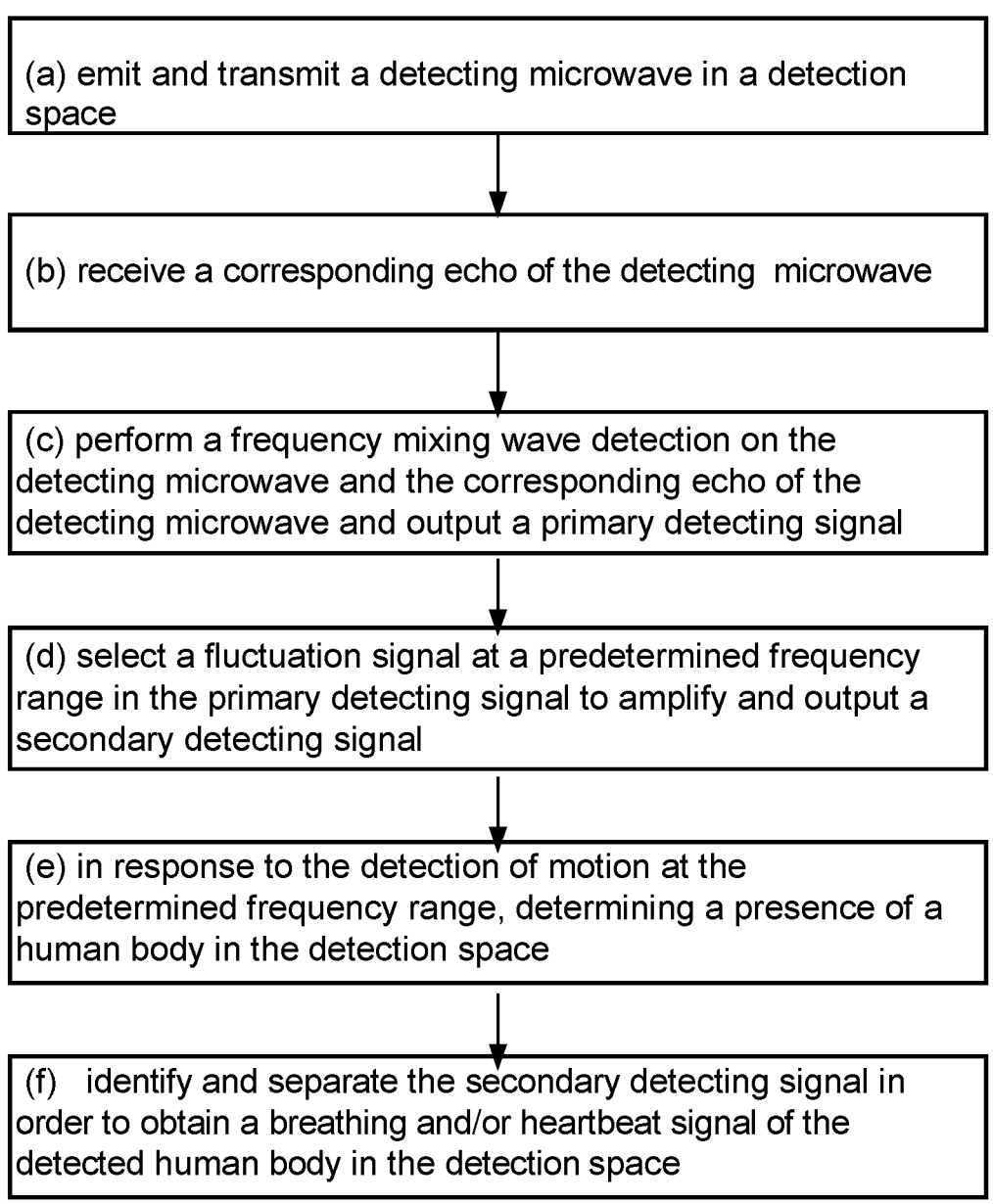
FIG. 11 is a procedural diagram illustrating the human presence detection method according to the above preferred embodiment of the present invention.

Referring to FIG. 11 of the drawings, a human presence detection method according to a preferred embodiment of the present invention is illustrated, wherein the method comprises the following steps.

(a) emitting and transmitting a detecting microwave in a detection space;

(b) receiving a corresponding echo of the detecting microwave;

(c) performing a frequency mixing wave detection on the detecting microwave and the corresponding echo of the detecting microwave and outputting a primary detecting signal; and (d) selecting and amplifying a fluctuation signal at a predetermined frequency range in the primary detecting signal to output a secondary detecting signal.

It is worth mentioning that, in the step (d), the predetermined frequency range is embodied as less than 3 Hz, wherein the secondary detecting signal is a response signal in responsive to any motion at a frequency less than 3 Hz detected in the detection space, so as to detect whether a human body is presented in the detection space in responsive to the breathing and/or heartbeat motion or motion of the human body.

Further, after the step (d), the method further comprises a step of:

(e) monitoring and detecting any fluctuation signal in the secondary detecting signal and determining a presence of the human (living) body when the fluctuation signal at the predetermined frequency range is contained in the secondary detecting signal.

Further, after the step (e), the method further comprises a step of:

(f) identifying and separating the secondary detecting signal, so as to obtain frequency signal corresponding to the breathing and heartbeat of the detected human body in the detection space.

Referring to FIGS. 5-10 of the drawings, a human presence detector according to another preferred embodiment of the present invention is illustrated, wherein the human presence detector comprises at least one microwave sensor 100 and a signal processor 40. In this preferred embodiment, the microwave sensor 100 is a sensor configured to emit and transmit a detecting microwave and to receive the corresponding echo of the detecting microwave. In particular, the detecting microwave emitted by the microwave sensor 100 preferably has a frequency of 24.125 G.

More specifically, the microwave sensor 100 comprises at least one microwave generator 10, at least one microwave receiver 20 and a frequency mixing wave detector 30, wherein the at least one microwave generator 10 is configured to emit and transmit a detecting microwave within a detection space. The at least one microwave receiver 20 is configured to receive the corresponding echo of the detecting microwave, wherein the frequency mixing wave detector 30 is linked to the at least one microwave generator 10 and the at least one microwave receiver 20 and is configured to perform a frequency mixing wave detection on the detecting microwave transmitted by the microwave generator 10 and the corresponding echo of the detecting microwave received by the at least one microwave receiver to output a corresponding detecting data.

It is worth mentioning that the detecting data outputted from the frequency mixing wave detector 30 is a direct response signal in responsive to one or more motions occurred in the detection space. In other words, the detecting microwave reflected by the human body (the corresponding echo) in the detection space will be received. It is appreciated that, according to different requirements, the detecting data is going to be targeted processed in order to obtain different detection result, while different control operations are performed according to the detection result according to different configurations.

For example, in the above preferred embodiment of the present invention, the detecting data obtained in the frequency mixing wave detector 30 is a primary detecting signal. In other words, the primary detecting signal is a response signal in response to the motions detected in the detection space. The signal processor 40 is linked to the frequency mixing wave detector 30 and is configured to select and amplify the primary detecting signal outputted by the frequency mixing wave detector 30, so as to select a fluctuation signal at a predetermined frequency range in the primary detecting signal to amplify and output a secondary detecting signal. Accordingly, the response signal of the motion at the predetermined frequency range is amplified by the human presence detector. In other words, the secondary detecting signal is signal that merely responds to the response signal at the predetermined frequency range of the motion, such that in response to the detection of the motions at the predetermined frequency range, the human presence detector determines that a human (living) body is presented in the detection space.

In addition, different analysis measures can be applied to the detecting data to obtain different detection results. Referring to the FIGS. 5-8 of the drawings, one processing method is illustrated. Accordingly, the microwave sensor 100 comprises a power-supply module 110 and a detection module 120, wherein the power-supply module 110 is configured to acquire external power source for the microwave sensor 100 and the signal processor 40 of the human presence detector, wherein the detection module 120 is configured to receive the reflected microwave as the detecting data. In other words, the detection module 120 is equivalent to the microwave receiver 20 and the frequency mixing wave detector 30 of the above preferred embodiment. The detecting data acquired by the detection module 120 is arranged to process in the signal processor 40. In particular, the purpose of the data processing according to the preferred embodiment is to detect the fluctuation signal with a frequency around 3 Hz, corresponding to the presence of the human body.

Those who skilled in the art would understand that the processing methods adopted by the signal processor 40 can be controllably selected or programmed according to different processing purposes. It should be pointed out that, according to this preferred embodiment, the processing method adopted by the signal processor refers to an extraction process to the corresponding echo of the detecting microwave transmitted by the microwave sensor 100. It is worth mentioning that the detecting microwaves of the microwave sensor 100 can be correlated with each other according to different detection requirements.

Figure 6:
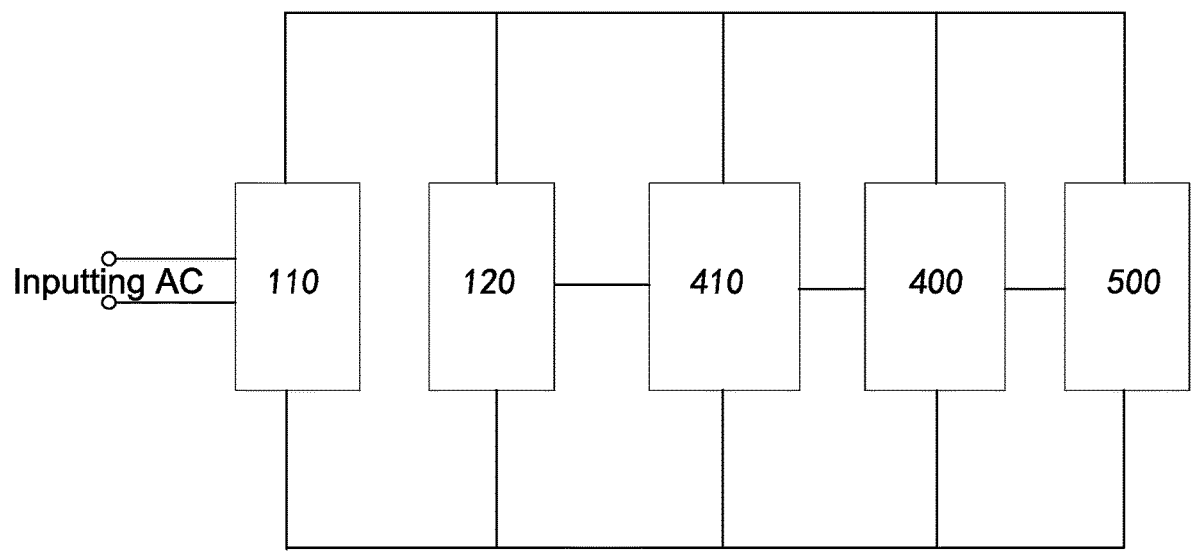
FIG. 6 is a procedural block diagram illustrating the human presence detector according to the above preferred embodiment of the present invention.

Referring to FIG. 6 of the drawings, the signal processor 40 according to the above preferred embodiment of the present invention is illustrated, wherein the signal processor 40 is communicatively linked with the microwave sensor 100. Accordingly, the signal processor 40 further comprises a central control unit 400 and a signal processing unit 410, wherein the central control unit 400 is arranged for receiving and processing the detecting data to obtain the detection result based on a preset goal and the signal processing unit 410 is configured to execute predetermined control operations based on the detection result.

In the preferred embodiment of the present invention, the human presence detector is further linked to an execution module 500 to indicate the detection results. Accordingly, the power-supply module 110 is arranged to supply electrical power to the detection module 120, the central control unit 400 and the signal processing unit 410. Preferably, the detection module 120 is embodied as a microwave Doppler detection module, which is configured to generate a difference signal between the detecting microwave and the corresponding echo of the detecting microwave according to the microwave Doppler effect principle. Then, the difference signal is processed in the signal processing unit 410. It should be pointed out that the signal processing unit 410 is incorporated with the central control unit 400 in the analysis of the detecting microwave, wherein the central control unit 400 is configured to execute predetermined control operations based on the detection result.

Preferably, the signal processing unit 410 in the preferred embodiment of the present invention is configured to detect a difference signal (such as a phase difference signal, frequency difference signal, and the like) between the detecting microwave and the corresponding echo of the detecting microwave according to the microwave doppler effect principle. In other words, the signal processing unit 410 is configured to detect the presence of human body in the detection space based on the difference signal detected by the detection module 120. Moreover, the temporal feature of the detection signal indicates the motion, action and/or movement variation detected in the detection space, such that the signal processor 40 is able to execute predetermined control operations based on the motion features detected in the detection space. For example, upon detecting an increase in the number of people in the detection space (such as a room), the signal processor 40 is arranged to brighten the lighting in the room. Similar operations can be previously set in the central control unit 400.

It is worth mentioning in order for reducing the distortion of the secondary detecting signal at the predetermined frequency range due to amplification and filtering operations, the signal processor 40 can be configured to perform a multistage selection and amplification to the acquired primary detecting signal, so as to select a fluctuation signal at a predetermined frequency range of in the primary detecting signal to amplify and output a secondary detecting signal. In other words, a plurality of the signal processing units 410 can be equipped in this embodiment. Alternatively, the signal processing unit 410 may further comprises a plurality of signal selection and/or signal processing components, wherein there is no intention of limiting the scope of the present invention.

More specifically, the signal processing unit 410 further comprises at least one signal amplifying unit 4101 and a wave filter 4102 linked with the signal amplifying unit 4101, wherein the signal amplifying unit 4101 is configured to amplify the difference signal in the detecting data (namely the primary detecting signal), and the wave filter 4102 is arranged to filter the amplified difference signal so as to output a detection result which can be determined in the central control unit 400.

Figure 5:
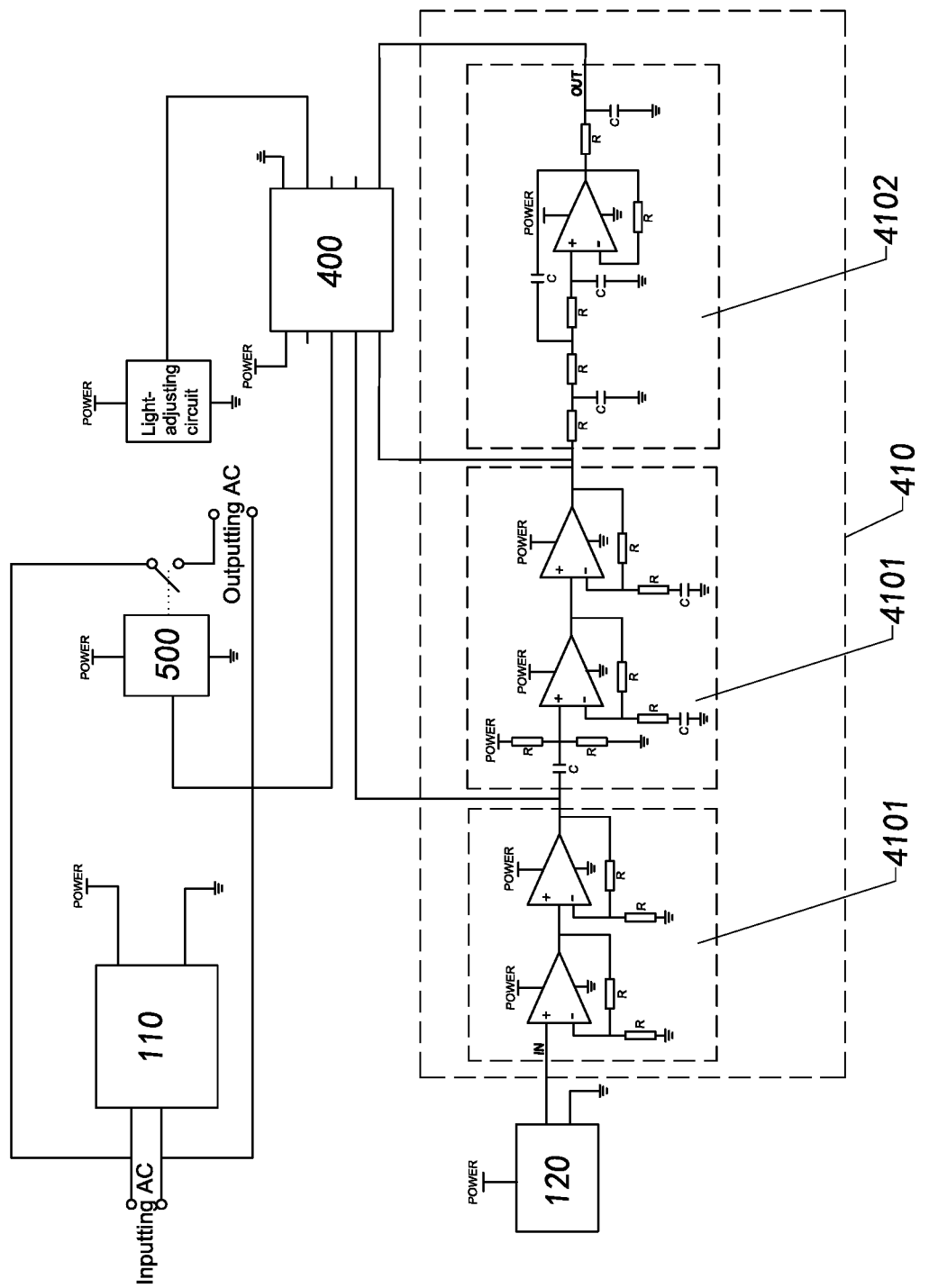
FIG. 5 is a block diagram illustrating a circuitry of the human presence detector according to the above preferred embodiment of the present invention.
Figure 7:
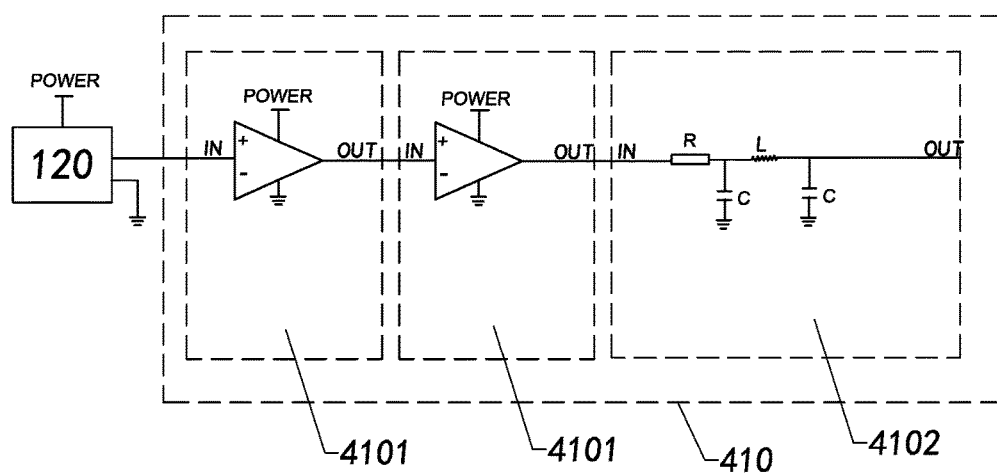
FIG. 7 is a schematic diagram illustrating a circuitry of a signal processor of the human presence detector according to the above preferred embodiment of the present invention.

Referring to FIG. 7 of the drawings, a circuit of the signal processing unit 410 according to one embodiment of the present invention is illustrated, wherein the signal processing unit 410 comprises a Level 1 DC amplification module, a Level 1 AC amplification module, and an analog filter. Referring to FIG. 5 of the drawings, a circuit of the signal processing unit 410 according to another embodiment of the present invention is illustrated, wherein the signal processing unit 410 comprises a Level 2 DC amplification module, a Level 2 AC amplification module, and an analog filter.

Those who skilled in the art would understand that the signal amplifying unit 4101 can be selected from a group consisting of DC amplification module of Level 1 and above, and AC amplification module of Level 1 and above, and the wave filter 4102 can be selected from a group consisting of analog filter and digital filter. The analog filter includes but not limited to low pass filter, high pass filter, band pass filter, band stop filter, dielectric filter, active filter, and passive filter. The digital filter is a filter that utilizes a universal computer programmed with required formulas and/or algorithms to perform a digital filtering action. For example, the digital filter comprises MCU, DSP, ARM or other necessary hardware elements to support running the corresponding algorithm, wherein the algorithms include, but are not limited to, Fourier transform (FFT/DFT) transform, Butterworth filter, and Kalman filter.

Accordingly, particular signal processing method is applied in processing the acquired detecting data in the preferred embodiment of the present invention. For example, the detection module 120 would acquire a detecting data, comprising a plurality of fluctuation signals, in responsive to the motions occurred in the detection space, wherein the detecting data has some features corresponding to features of the motions in the detection space. For instance, if one thousand fluctuation signals are detected in one second at the detection module 120, the signal amplifying unit 4101 may perform an enveloping operation to the detecting data, i.e., coupling the one thousand fluctuation signals into a new microwave (the amplified microwave). Then, the amplified microwave is filtered by the wave filter 4102. For example, the wave filter 4102 is configured to select the fluctuation signal with a frequency less than 3 Hz, and to filter the fluctuation signal with a frequency greater than 3 Hz. It should be pointed out that the number of motions occurring within one second in the detection space corresponds to the total number of fluctuations. As such, the detection result is obtained eventually. It is worth mentioning that the circuit of the signal processing unit 410 is limited and determined by the central control unit 400 according to the preferred embodiment of the present invention.

In particular, when the wave filter 4102 is embodied as a digital filter which is preferably integrated in the central control unit 400, the central control unit 400 further comprises a signal sampling module, a digital filtering module, a program center, and at least one inputting and outputting interface. The central control unit 400 is arranged to specifically process the detecting data to acquire a detection result based on different purposes or requirements. The inputting and outputting interface executes according to a determination basis preset in the program center detection result. Further, corresponding control signal is outputted from the central control unit 400 to the execution module for specific operations.

Figure 8:
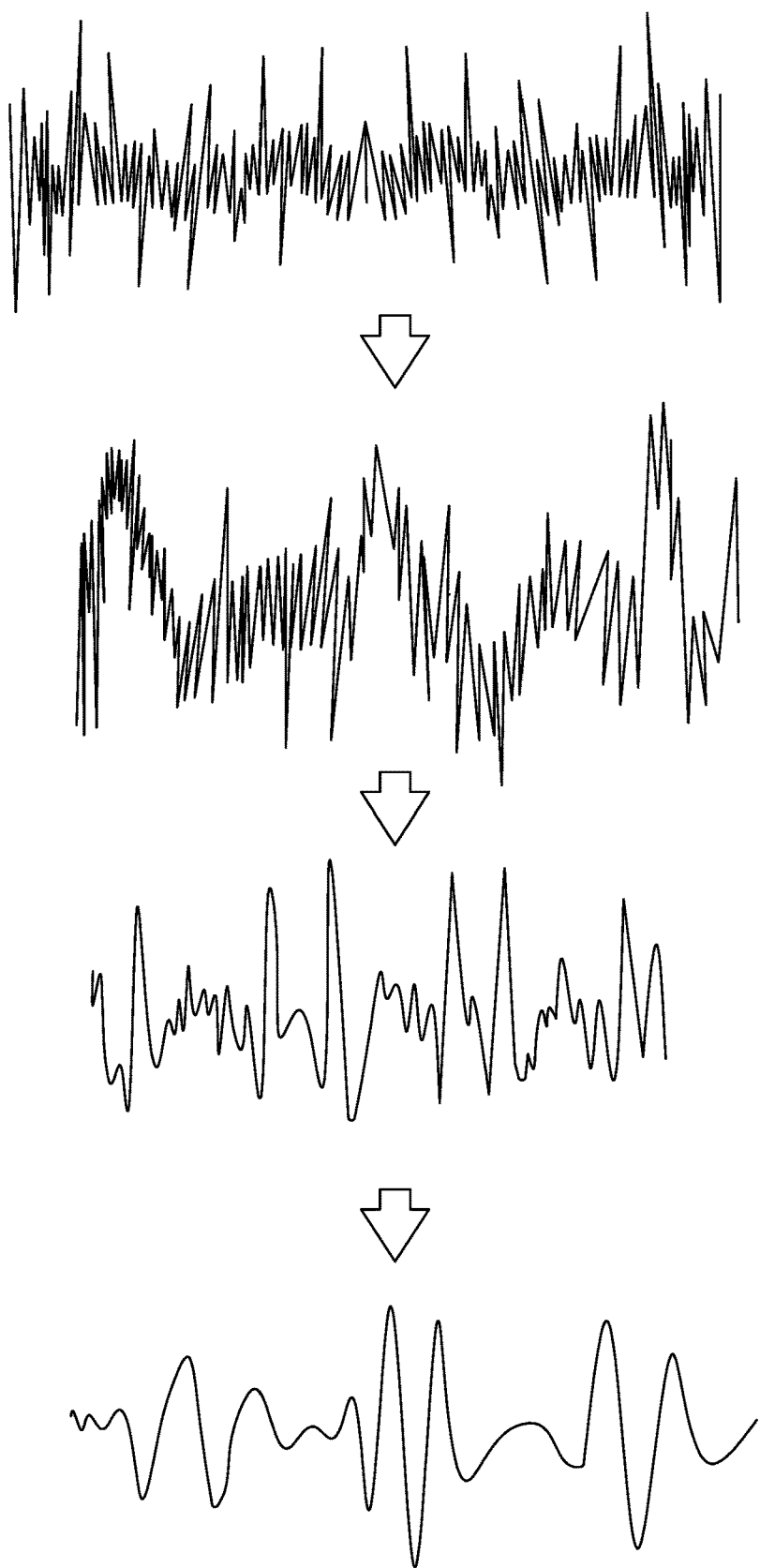
FIG. 8 is an oscillograph of a detecting microwave and microwaves during a signal processing process of the human presence detector according to the above preferred embodiment of the present invention.

Referring to FIG. 8 of the drawings, a process of processing the detecting data into a detection result according to the above preferred embodiment of the present invention is illustrated. Accordingly, the volume of the detecting data acquired at the signal processing unit 410 is very large, and the detecting data is analyzed according to the requirements of the human presence detection in the preferred embodiment. Preferably, as illustrated in the FIG. 8 of the drawings, the detecting data is firstly processed by a two-stage DC amplification module, and then being processed by a two-stage AC amplification module in order for amplifying and selecting the detecting data. Then, a detection result, which is determinable, is extracted from amplified detecting data. Then, respective control is performed according to the pre-programmed instructions. It is worth mentioning that, except for the aforementioned circuit, the analysis to the detecting data can also be processed by at least one signal amplifying unit 4101 (such as DC amplification module, AC amplification module) and at least one filter 4102 (such as digital filter, analog filter). In order to fully illustrate the application environment of the human presence detector, the application scenario is illustrated in the FIG. 9 of the drawings is taken as an example.

Figure 9:
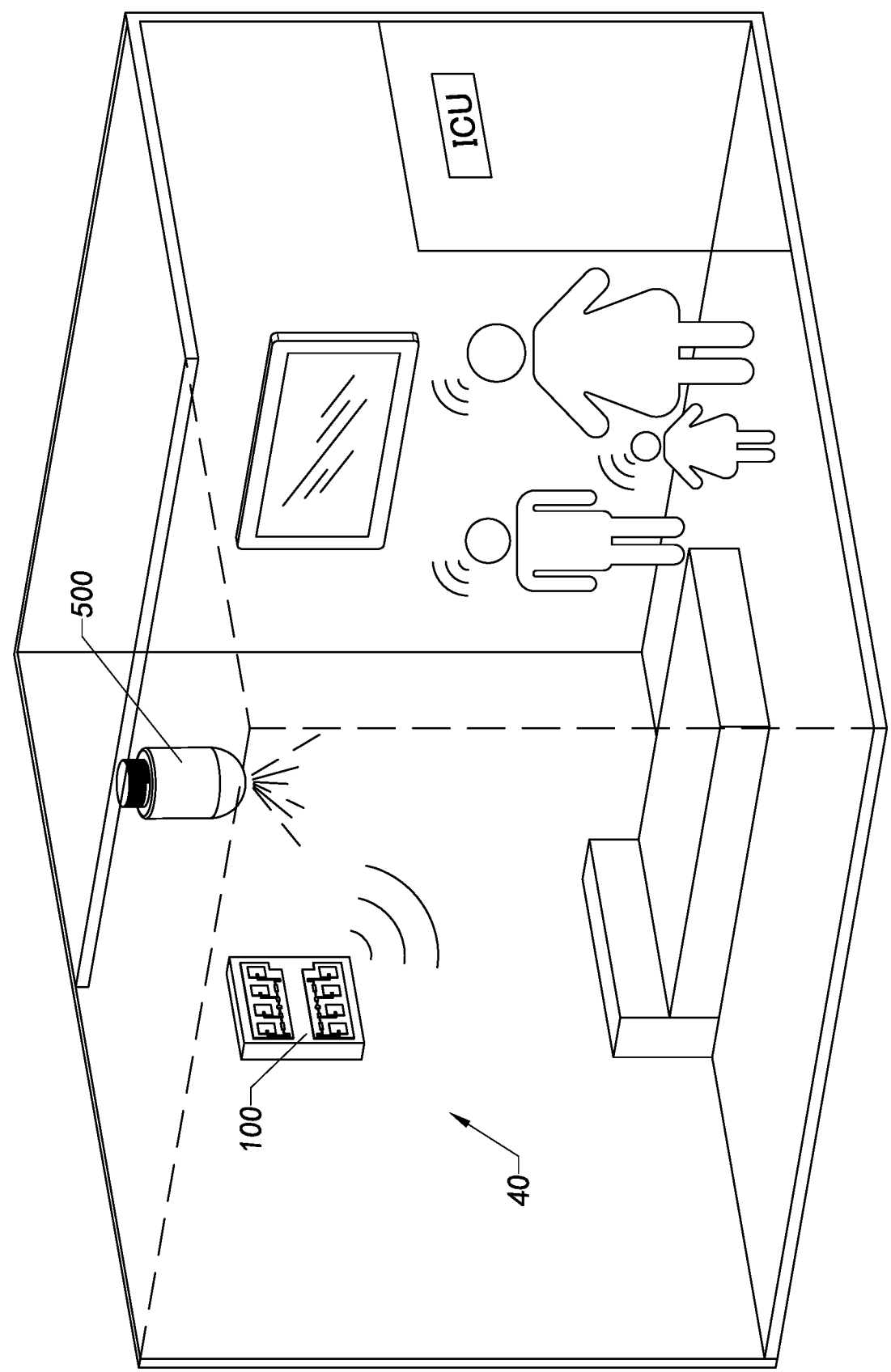
FIG. 9 is a schematic diagram illustrating an application of the human presence detector according to the preferred embodiment of the present invention.

As illustrated in the FIG. 9 of the drawings, the microwave sensor 100 of the human presence detector is disposed in the detection space and facing towards the internal environment of the detection space for receiving the reflected microwave (corresponding echo) of a detecting microwave, wherein, preferably, the microwave sensor 100 is configured to emit and transmit the detecting microwave. Of course, the detecting microwave can be emitted and transmitted by one or more other devices in other preferred embodiments of the present invention. Once the detecting microwave is reflected by a human body, the detecting data (namely the reflected detecting microwave) acquired by the detection module 120 has a difference with the transmitted detecting microwave. Then, the detecting data is processed and analyzed by the signal processing unit 410 to output a detection result for the central control unit 400. In this application scenario, the reflection data of three human bodies are detected by the detection module 120 and the signal processing unit 410 is configured to process the detecting data according to the instructions programmed in the central control unit 400, so as to obtain a detection result regarding the presence of the human bodies in the detection space. Accordingly, according to the detection result regarding to the presence the human bodies in the detection space, the central control unit 400 acquires a result that three human bodies are existed in the detection space, wherein the detection result is further used to adjust a control signal of the execution module 500. For example, the control signal can be a signal to adjust a brightness of an illuminating light according to the detection result of the number of people in the detection space or adjust an angle of the illuminating light according to the positions of the detected people in the detection space.

Figure 10:
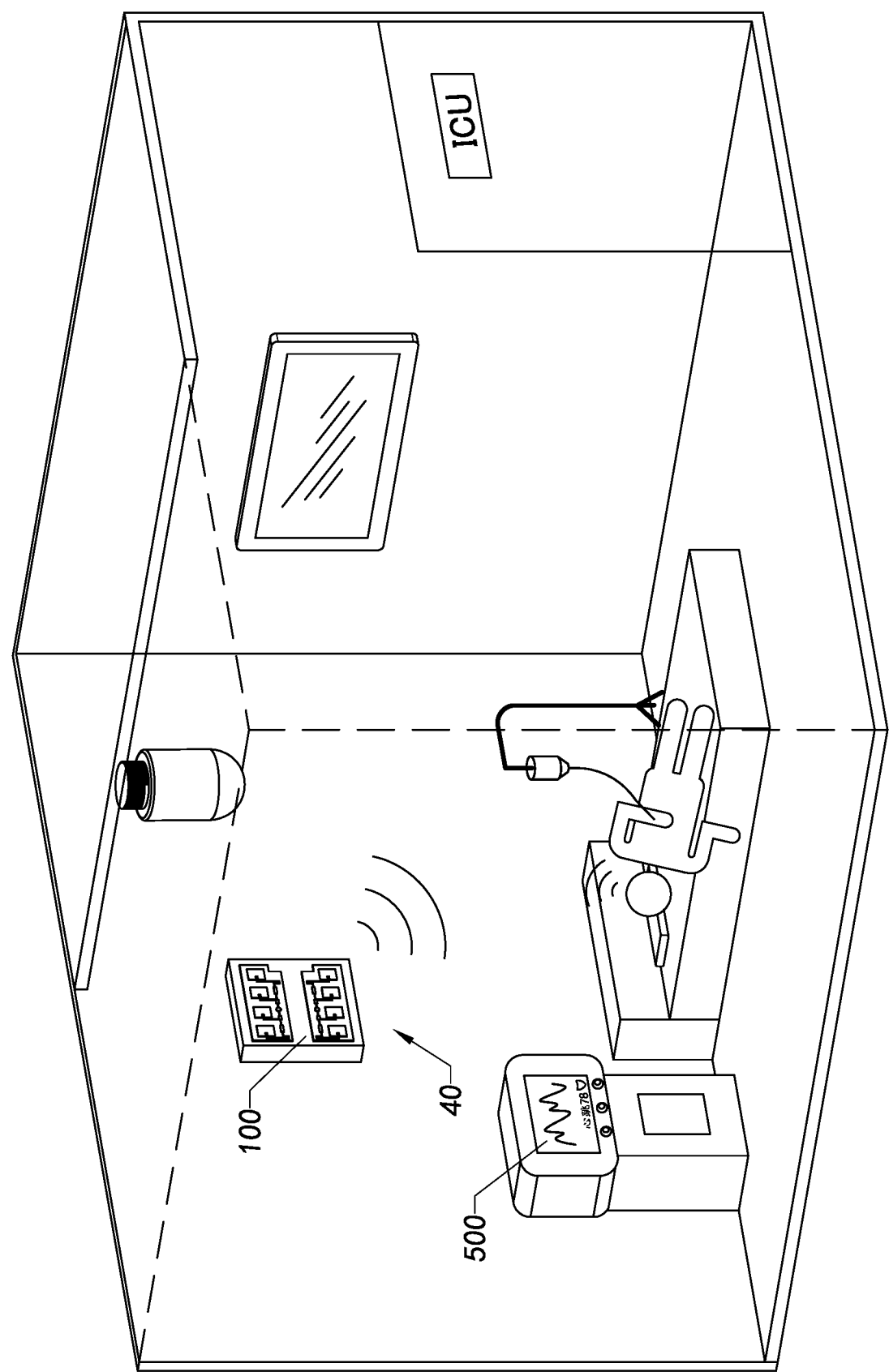
FIG. 10 is another schematic diagram illustrating another application of the human presence detector according to the preferred embodiment of the present invention.

Moreover, in the application scenario as illustrated in the FIG. 10 of the drawings, the human presence detector not only can obtain the information of the presence of the human body in the detection space, but also can obtain health information of the detected human body in the detection space. For example, the microwave sensor 100 of the human presence detector is disposed in the detection space, such as the ICU, intensive care unit, in a hospital, and facing towards the internal environment of the detection space to receive the reflected detecting microwave. It is worth mentioning that the detecting microwave having a special frequency feature that won't interfere with the radiation microwave generated by other electrical appliances or communication devices. Once the detecting microwave is reflected by a human body, the detecting data (namely the reflected detecting microwave) obtained in the detection module 120 has a difference with the transmitted detecting microwave. In this application scenario, the reflected data of the human body obtained in the detection module 120 and the detecting data also contain data responsive to the heartbeats of the detected human body in the detection space. The detecting data is processed and analyzed by the signal processing unit 410 to output a detection result for the central control unit 400, that is, the signal processing unit 410 is configured to process the detecting data according to the instructions programmed in the central control unit 400 so as to obtain a detection result regarding to the target, such the presence or the heartbeat of the human body, required by the central control unit 400. That is the signal processing unit 410 obtains the detection result regarding the presence and human information of the human body in the detection space according to instruction of the central control unit 400. In other words, compared with the aforementioned application as illustrated in the FIG. 9 of the drawings, this application scenario provides further analyzation according to the detection result regarding to the presence of the human body obtained in the central control unit 400 and the control signal of the execution module 500 is adjusted. For example, the heartbeat data of the detected human body based on the detection result of the number of people are displayed, wherein the health status of the detected human body can be detection result truly reflected in real-time according to the microwave data reflected by the detected human body, without adding and intervening of additional human monitoring equipment.

Referring to FIG. 11 of the drawings, a human presence detecting method according to the above preferred embodiment of the present invention is illustrated, wherein the method comprises the following steps. Firstly, a detecting microwave is emitted and transmitted into a detection space. Those who skilled in the art would understand that the detecting microwave at a special frequency won't have any interference with communication signals and won't affect the normal communication in the detection space. Then, a corresponding echo of the detecting microwave is received. According to a difference between the transmitted detecting microwave and the received corresponding echo of the detecting microwave, detecting data is obtained, i.e. the primary detecting signal. According to the requirements, the detecting data are entirely or partially selected to amplify and to perform a wave filtration, so as to extract a detection result therefrom, i.e. the secondary detecting signal. Accordingly, the detection result indicates some features in the detection space. For example, a detection result of the presence of human body in the detection space is obtained according to fluctuation signal with a frequency around 3 Hz. And, by further analyzing the features in the detection result, the secondary detecting signal is separated to finally obtain the determination of the presence of human body in the detection space as well as the data of human breathing and/or heartbeat of the detected human body in the detection space.

It is worth mentioning that, according to differences between the amplitude intervals and the frequency intervals of the fluctuation signals corresponding to the breathings and heartbeats of different human (living) bodies, the fluctuation signals corresponding to the breathings and heartbeats of different human (living) bodies in the detection space can be identified and separated, so as to simultaneously monitor and detect the breathing and/or heartbeat statuses of different human bodies detected in the detection space and to obtain the total number of the detected human bodies in the detection space at the same time. In addition, based on the difference between the amplitude intervals and the frequency intervals of the fluctuation signals corresponding to the breathings and heartbeats of different human (living) bodies, the fluctuation signal corresponding to the breathing and heartbeat of each specific human (living) body in the detection space can be identified and separated, so that the human presence detector of the present invention can thus monitor and detect the breathing and/or heartbeat status of each of the human bodies detected in the detection space according to the corresponding amplitude and frequency of the separated fluctuation signal.

More specifically, in view of the facts that the breathing frequency of a healthy human being will not exceed 60 times per minute (i.e. 1 Hz), and the heartbeat rate of a healthy human being will not be less than 60 times per minute and will not exceed 180 times per minute (i.e. greater than 1 Hz and less than 3 Hz), when the parameters of the wave filter 4102 of the signal processing unit 410 are set at a value that that the wave filter 4102 is able to filter out fluctuation signal(s) with a frequency of 1 Hz or less, the fluctuation signal in the secondary detection signal is directed as breathing frequency signal corresponding to the breathing features of the detected human body, and that when the parameters of the wave filter 4102 of the signal processing unit 410 are set at a value that that the wave filter 4102 is able to filter out fluctuation signal(s) with frequency(s) greater than 1 Hz and less than 3 Hz, the fluctuation signal detected in the secondary detection signal is directed as heartbeat frequency signal corresponding to the heartbeat features of the detected human body. Accordingly, the separation of the fluctuation signal(s) corresponding to the breathing(s) and heartbeat(s) of the detected human body(ies) in the secondary detecting signal can be implemented.

In other words, with multiple wave filters 4102 with difference parameters respectively, or with one wave filter having the setting of difference parameters, the fluctuation signals corresponding to the breathings and heartbeats of different human (living) bodies in the detection space can be identified and separated from the secondary detecting signal, and the fluctuation signal corresponding to the breathing and heartbeat of a specific human (living) body in the detection space can also be identified and separated from the secondary detecting signal.

It is appreciated that, the detection of the breathings and/or heartbeats of different human (living) bodies in the detection space, or the detection of the breathing and/or heartbeat of the same person in the detection space as suggested in the present invention is not limited to the applications of the human presence detector as mentioned above and shown in FIGS. 9 and 10. Practically, the human presence detector of the present invention is capable of applying in intelligent home system and intelligent security system for arranging and adjusting the environment of the detected human body according to the detection result regarding the breathing and/or heartbeat of human body, for controlling and adjusting the lighting, air-conditioning, temperature, humidity, and etc. of the environment of the detected human body according to the detection result regarding the breathing and/or heartbeat status of the detected human body, and for determining whether the detect the fatigue or lassitude of the human body during driving according to the detecting data regarding the breathing and/or heartbeat of the detected human body. It would also be appreciated to apply the human presence detector of the present invention in sleeping quality control and monitoring as well as sleeping induction and etc. by monitoring and detecting the breathing and/or heartbeat of human body in the detection space and produce the detection result thereof for operating and controlling of relative equipment and appliance.

In particular, the processing to the secondary detection signal can be delayed in order to eliminate the interference of sporadic motions with a frequency less than 3 Hz according to the cyclical characteristic of the fluctuation signal corresponding to the breathing and the heartbeat of the human body, thereby improving the reliability of the detection of the breathing and/or heartbeat status of the human body.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A human presence detector for determining a presence of human body in response to respiratory motion and heartbeat motion and identifying different human bodies in response to different respiratory motions and heartbeat motions in real-time in a detection space which is non-movable, comprising:
   a microwave generator configured to emit and transmit a detecting microwave in the detection space;
   a microwave receiver configured to receive a corresponding echo of said detecting microwave;
   a frequency mixing wave detector, which is linked to said microwave generator and said microwave receiver and configured to perform a frequency mixing wave detection on said detecting microwave emitted and transmitted by said microwave generator and said corresponding echo of said detecting microwave received by said microwave receiver, wherein according to a difference between said detecting microwave transmitted and said corresponding echo received, detecting data is obtained and outputted as a primary detecting signal which is a response signal of the respiratory motion and the heartbeat motion detected in the detection space; and
   a signal processor, which is linked to said frequency mixing wave detector, comprising a signal processing unit which comprises at least one signal amplifying unit and one or more wave filters linked with said at least one signal amplifying unit, wherein said at least one signal amplifying unit is configured to amplify said primary detecting signal outputted by said frequency mixing wave detector to form an amplified primary detecting signal and said wave filter is configured to select and filter one or more fluctuation signals each having a frequency equal to or less than 3 Hz in said primary detecting signal to amplify and to output a secondary detecting signal having the frequency equal to or less than 3 Hz while each of said fluctuation signals with a frequency greater than 3 Hz is filtered from said primary detecting signal by said one or more wave filters so as for reducing any interference of environmental motion, action and movement in the detection space, wherein when parameter of said one or more wave filters is set as a value that said one or more fluctuation signals corresponding to the respiratory motion and the heartbeat motion and when said one or more fluctuation signals at the frequency equal to or less than 3 Hz are detected in said secondary detecting signal in real-time, said response signal corresponding to the respiratory motion and the heartbeat motion detected in the detection space in real-time with the frequency equal to or less than 3 Hz is amplified for determination of a presence of human body in response to the respiratory motion and the heartbeat motion of the detected human body in the detection space, wherein when different parameters of said one or more wave filters are set as values that said one or more fluctuation signals corresponding to the respiratory motions and the heartbeat motions of different human bodies in the detection space in real-time, the different human bodies are identified and separated from said secondary detecting signal and said one or more fluctuation signals are also identified and separated from said secondary detecting signal.

2. The human presence detector, as recited in claim 1, wherein according to differences between amplitude intervals and frequency intervals of said fluctuation signals of said secondary detecting signal corresponding to breathings and heartbeats of different human bodies, said one or more fluctuation signals corresponding to the respiratory motion and the heartbeat motion of a specific human body of the human bodies in the detection space is identified and separated so as to monitor conditions and statuses of the breathings and the heartbeats of each of the human bodies detected in the detection space in a real time basis according to the amplitude and the frequency of said corresponding fluctuation signal being separated.

3. The human presence detector, as recited in claim 1, wherein said microwave generator and said microwave receiver are configured together as a microwave sensor adapted to emit and transmit said detecting microwave and receive said corresponding echo of said detecting microwave.

4. The human presence detector, as recited in claim 3, wherein said frequency mixing wave detector is integrated in said microwave sensor.

5. A human presence detector for determining a presence of human body in response to respiratory motion and heartbeat motion and identifying different human bodies in response to different respiratory motions and heartbeat motions in real-time in a detection space which is non-movable, comprising:

a microwave sensor which is configured to emit and transmit a detecting microwave in the detection space, and to receive a corresponding echo of said detecting microwave, wherein said microwave sensor is further configured to perform a frequency mixing wave detection on said detecting microwave emitted and transmitted by said microwave generator and said corresponding echo of said detecting microwave received by said microwave receiver, wherein according to a difference between said detecting microwave transmitted and said corresponding echo received, detecting data is obtain and outputted as a primary detecting signal which is a response signal of the respiratory motion and the heartbeat motion detected in the detection space; and a signal processor, which is linked to said microwave sensor, comprising a signal processing unit which comprises at least one signal amplifying unit and one or more wave filters linked with said at least one signal amplifying unit, wherein said at least one signal amplifying unit is configured to amplify said primary detecting signal outputted by said frequency mixing wave detector to form an amplified primary detecting signal and said wave filter is configured to select and filter one or more fluctuation signals each having a frequency equal to or less than 3 Hz in said primary detecting signal to amplify and to output a secondary detecting signal having the frequency equal to or less than 3 Hz while each of said fluctuation signals with a frequency greater than 3 Hz is filtered from said primary detecting signal by said one or more wave filters so as for reducing any interference of environmental motion, action and movement in the detection space, wherein when parameter of said one or more wave filters are set as a value that said one or more fluctuation signals corresponding to the respiratory motion and the heartbeat motion and when said one or more fluctuation signals at the frequency equal to or less than 3 Hz are detected in said second detecting signal in real-time, said response signal corresponding to the respiratory motion and the heartbeat motion detected in the detection space in real-time with the frequency equal to or less than 3 Hz is amplified for determination a presence of human body in response to the respiratory motion and the heartbeat motion of the detected human body in the detection space, wherein when different parameters of said one or more wave filters are set as values that said one or more fluctuation signals corresponding to the respiratory motions and the heartbeat motions of different human bodies in the detection space in real-time, the different human bodies are identified and separated from said secondary detecting signal and said one or more fluctuation signals are also identified and separated from said secondary detecting signal.

6. The human presence detector, as recited in claim 5, wherein according to differences between amplitude intervals and frequency intervals of said fluctuation signals in said secondary detecting signal corresponding to breathings and heartbeats of different human bodies, said one or more fluctuation signals corresponding to the respiratory motion and the heartbeat motion of a specific human body of the human bodies in the detection spaced is identified and separated so as to monitor conditions and statuses of the breathings and the heartbeats of each of the human bodies detected in the detection space in a real time basis according to corresponding the amplitude and the frequency of said fluctuation signal being separated.

7. The human presence detector, as recited in claim 6, wherein said microwave sensor further comprises a power-supply module acquiring at least one external power source for said at least one microwave generator and said at least one microwave receiver and a detection module receiving said reflected detecting microwave as detecting data.

8. The human presence detector, as recited in claim 7, wherein said signal processor further comprises a central control unit and a signal processing module, wherein said signal processing module receiving and processing said detecting data from said detection module to said detection result to be determinable, wherein said central control unit is preset with programs for obtaining said detection result and processing said detecting data.

9. The human presence detector, as recited in claim 8, wherein said detection module is a microwave-doppler detection module.

10. The human presence detector, as recited in claim 8, wherein said signal processor comprises at least one signal amplifying unit and at least one wave filter.

11. The human presence detector, as recited in claim 10, wherein said signal amplifying unit is selected from a group consisting of DC amplification module and AC amplification module.

12. The human presence detector, as recited in claim 10, wherein said wave filter is selected from a group consisting of analog filter and digital filter.

13. The human presence detector, as recited in claim 12, wherein the analog filter is selected from a group consisting of low pass filter, high pass filter, band pass filter, band stop filter, dielectric filter, active filter, and passive filter.

14. The human presence detector, as recited in claim 12, wherein said digital filter is selected from a hardware group consisting of MCU, DSP and ARM to support running corresponding algorithm which is selected from a group consisting of Fourier transform (FFT/DFT) transform, Butterworth filter, and Kalman filter.

15. The human presence detector, as recited in claim 8, wherein said central control unit comprises a signal sampling module, a digital filtering module, a program center, and at least one inputting and outputting interface, wherein different program instructions corresponding to different requirements are stored in said program center, wherein said signal sampling module and said digital filtering module are configured to process said detecting data so as to obtain said detection result, wherein comparison basis is preset in said program center, and said inputting and outputting interface is configured to execute said detection result.

16. A method of detecting a presence of human body in a detection space which is non-movable in response to respiratory motion and heartbeat motion and identifying different human bodies in response to different respiratory motions and heartbeat motions in real-time, comprising steps of:
  (a) emitting and transmitting a detecting microwave in a said detection space;
  (b) receiving a corresponding echo of the detecting microwave;
  (c) performing a frequency mixing wave detection on said detecting microwave and said corresponding echo of said detecting microwave to output a primary detecting signal;
  (d) detecting and selecting one or more fluctuation signals each having a frequency equal to or less than 3 Hz in said primary detecting signal to amplify so as to output a secondary detecting signal having the frequency equal to or less than 3 Hz while each of said fluctuation signals with a frequency greater than 3 Hz is filtered from said primary detecting signal so as for reducing any interference of environmental motion, action and movement in the detection space, wherein said secondary detecting signal is a response signal in response to a respiratory motion and a heartbeat motion at a frequency less than 3 Hz detected in said detection space according to a difference between said detecting microwave transmitted and said corresponding echo received;
  (e) monitoring said one or more fluctuation signals of said secondary detecting signal determining a presence of a human body in response to the respiratory motion and the heartbeat motion of the detected human body in said detection space when said secondary detecting signal has one or more of said fluctuation signals at the frequency equal to or less than 3 Hz in real-time, and filtering each of said fluctuation signals with a frequency greater than 3 Hz from said primary detecting signal so as for reducing any interference of environmental motion, action and movement in the detection space; and
  (f) according to differences between amplitude intervals and frequency intervals of said fluctuation signals of said secondary detecting signal corresponding to breathings and heartbeats of different human bodies, identifying and separating said one or more fluctuation signals corresponding to the respiratory motion and the heartbeat motion of a specific human body of the human bodies in the detection space, so as to monitor conditions and statuses of the breathings and the heartbeats of each of the human bodies detected in the detection space in a real time basis according to the amplitude and the frequency of said corresponding fluctuation signal being separated and to obtain a breathing frequency signal and a heartbeat frequency signal of the specific human body detected in the detection space.

17. The human presence detection method, as recited in claim 16, wherein the step (f) further comprises the steps of:
  identifying and separating said fluctuation signal having a frequency less than 1 Hz in said secondary detecting signal, wherein said fluctuation signal in said secondary detecting signal at the frequency less than 1 Hz is directed as the breathing frequency signal of the human body detected in the detection space; and
  identifying and separating said fluctuation signal at having a frequency greater than 1 Hz and less than 3 Hz in said secondary detecting signal, wherein the said fluctuation signal in said secondary detecting signal at frequency greater than 1 Hz and less than 3 Hz is directed as the heartbeat frequency signal of the human body detected in said detection space.

* * * * *